(12) United States Patent
Redei

(10) Patent No.: US 10,233,501 B2
(45) Date of Patent: *Mar. 19, 2019

(54) BIOMARKERS PREDICTIVE OF PREDISPOSITION TO DEPRESSION AND RESPONSE TO TREATMENT

(71) Applicant: Northwestern University, Evanston, IL (US)

(72) Inventor: Eva E. Redei, Chicago, IL (US)

(73) Assignee: Northwestern University, Evanston, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/727,174

(22) Filed: Oct. 6, 2017

(65) Prior Publication Data

US 2018/0030538 A1    Feb. 1, 2018

Related U.S. Application Data

(60) Continuation-in-part of application No. 14/598,970, filed on Jan. 16, 2015, now abandoned, and a continuation-in-part of application No. 15/296,807, filed on Oct. 18, 2016, now Pat. No. 9,951,387, which is a continuation of application No. 14/994,802, filed on Jan. 13, 2016, now Pat. No. 9,469,875, which is a division of application No. 13/276,565, filed on Oct. 19, 2011, now abandoned.

(60) Provisional application No. 61/394,449, filed on Oct. 19, 2010, provisional application No. 61/928,723, filed on Jan. 17, 2014.

(51) Int. Cl.
*G01N 33/68* (2006.01)
*C12Q 1/6883* (2018.01)

(52) U.S. Cl.
CPC ....... *C12Q 1/6883* (2013.01); *G01N 33/6893* (2013.01); *C12Q 2600/156* (2013.01); *C12Q 2600/158* (2013.01); *C12Q 2600/16* (2013.01); *G01N 2800/304* (2013.01); *G01N 2800/60* (2013.01)

(58) Field of Classification Search
None
See application file for complete search history.

(56) References Cited

U.S. PATENT DOCUMENTS

| | | |
|---|---|---|
| 5,011,769 A | 4/1991 | Duck et al. |
| 5,124,246 A | 6/1992 | Urdea et al. |
| 5,130,238 A | 7/1992 | Malek et al. |
| 5,210,884 A | 5/1993 | Redford |
| 5,270,184 A | 12/1993 | Walker et al. |
| 5,283,174 A | 2/1994 | Arnold, Jr. et al. |
| 5,288,609 A | 2/1994 | Engelhardt et al. |
| 5,399,491 A | 3/1995 | Kacian et al. |
| 5,403,711 A | 4/1995 | Walder et al. |
| 5,409,818 A | 4/1995 | Davey et al. |
| 5,455,166 A | 10/1995 | Walker |
| 5,538,848 A | 7/1996 | Livak et al. |
| 5,624,802 A | 4/1997 | Urdea et al. |
| 5,660,988 A | 8/1997 | Duck et al. |
| 5,695,934 A | 12/1997 | Brenner |
| 5,710,029 A | 1/1998 | Ryder et al. |
| 5,710,264 A | 1/1998 | Urdea et al. |
| 5,714,330 A | 2/1998 | Brenner et al. |
| 5,750,341 A | 5/1998 | Macevicz |
| 5,792,614 A | 8/1998 | Western et al. |
| 5,814,447 A | 9/1998 | Ishiguro et al. |
| 5,824,518 A | 10/1998 | Kacian et al. |
| 5,846,717 A | 12/1998 | Brow et al. |
| 5,849,481 A | 12/1998 | Urdea et al. |
| 5,851,770 A | 12/1998 | Babon et al. |
| 5,882,867 A | 3/1999 | Ullman et al. |
| 5,914,230 A | 6/1999 | Liu et al. |
| 5,925,517 A | 7/1999 | Tyagi et al. |
| 5,928,862 A | 7/1999 | Morrison |
| 5,958,692 A | 9/1999 | Cotton et al. |
| 5,985,557 A | 11/1999 | Prudent et al. |
| 5,994,069 A | 11/1999 | Hall et al. |
| 6,001,567 A | 12/1999 | Brow et al. |
| 6,013,170 A | 1/2000 | Meade |
| 6,063,573 A | 5/2000 | Kayyem |
| 6,090,543 A | 7/2000 | Prudent et al. |
| 6,110,677 A | 8/2000 | Western et al. |
| 6,110,684 A | 8/2000 | Kemper et al. |
| 6,121,001 A | 9/2000 | Western et al. |
| 6,150,097 A | 11/2000 | Tyagi et al. |
| 6,183,960 B1 | 2/2001 | Lizardi |

(Continued)

FOREIGN PATENT DOCUMENTS

| | | |
|---|---|---|
| WO | WO 00/018957 | 4/2000 |
| WO | WO 2006084132 | 8/2006 |

OTHER PUBLICATIONS

The Mammalian Gene Collection (https://genecollections.nci.nih.gov/MGC/ last updated Mar. 2009 and accessed online Oct. 23, 2018).*
Adessi et al., Solid phase DNA amplification: characterisation of primer attachment and amplification mechanisms, Nucleic Acid Res. 2010; 28:E87.
Altamura et al., Age at onset and latency to treatment (duration of untreated illness) in patients with mood and anxiety disorders: a naturalistic study. Int Clin Psychopharmacol 2010; 25: 172-9.
Andrus et al., Gene expression patterns in the hippocampus and amygdala of endogenous depression and chronic stress models. Molecular psychiatry 2012; 17: 49-61.
Barnay, Genetic disease detection and DNA amplification using cloned thermostable ligase, Proc. Natl. Acad. Sci USA 1991; 88:189-93.

(Continued)

*Primary Examiner* — Amanda Haney
(74) *Attorney, Agent, or Firm* — Casimir Jones SC; David W. Staple

(57) ABSTRACT

The present invention relates generally to the identification of subjects with a predisposition to recurrent depression, predicting a subject's responsiveness to therapy, and determining whether a subject has remitted from depression following therapy. In particular, provided herein are biomarkers, methods, and kits for such uses.

18 Claims, No Drawings

(56) References Cited

U.S. PATENT DOCUMENTS

| | | |
|---|---|---|
| 6,221,583 B1 | 4/2001 | Kayyem et al. |
| 6,235,502 B1 | 5/2001 | Weissman et al. |
| 6,248,229 B1 | 6/2001 | Meade |
| 6,303,305 B1 | 10/2001 | Wittwer et al. |
| 6,306,597 B1 | 10/2001 | Macevicz |
| 6,432,360 B1 | 8/2002 | Church |
| 6,485,944 B1 | 11/2002 | Church et al. |
| 6,511,803 B1 | 1/2003 | Church et al. |
| 6,534,274 B2 | 3/2003 | Becker et al. |
| 6,541,205 B1 | 4/2003 | Yokoyama et al. |
| 6,787,308 B2 | 9/2004 | Balasubramanian et al. |
| 6,833,246 B2 | 12/2004 | Balasubramanian |
| 7,323,305 B2 | 1/2008 | Leamon et al. |
| 7,374,885 B2 | 5/2008 | Becker et al. |
| 8,679,789 B2 | 3/2014 | Arnold et al. |
| 2005/0042638 A1 | 2/2005 | Arnold et al. |
| 2005/0130173 A1 | 6/2005 | Leamon et al. |
| 2006/0046265 A1 | 3/2006 | Becker et al. |
| 2012/0094859 A1 | 4/2012 | Redei |
| 2015/0218639 A1 | 8/2015 | Redei |
| 2015/0225792 A1 | 8/2015 | Redei |

OTHER PUBLICATIONS

Belmaker et al., Major depressive disorder. The New England journal of medicine 2008; 358: 55-68.

Belzeaux et al., Responder and nonresponder patients exhibit different peripheral transcriptional signatures during major depressive episode. Transl Psychiatry. Nov. 13, 2012;2:e185.

Benjamini et al., Controlling the False Discovery Rate—a Practical and Powerful Approach to Multiple Testing. J Roy Stat Soc B Met 1995; 57: 289-300.

Carter et al., The relationship of demographic, clinical, cognitive and personality variables to the discrepancy between self and clinician rated depression. J Affect Disord 2010; 124: 202-6.

Chinnaiyan et al., Mechanisms of enhanced radiation response following epidermal growth factor receptor signaling inhibition by erlotinib (Tarceva), Cancer Res 2005; 65:3328-35.

Cohen, Statistical Power Analysis for the Behavioral Sciences. 2nd ed. Hillsdale: L Erlbaum Associates; 1988, TOC only, 4 pages.

Cross-Disorder Group of the Psychiatric Genomics Consortium. Identification of risk loci with shared effects on five major psychiatric disorders: a genome-wide analysis. Lancet 2013; 381:1371-9.

Cuijpers et al., The effects of psychotherapies for major depression in adults on remission, recovery and improvement: A meta-analysis. J Affect Disorders 2014; 159:118-126.

Desmond et al., The Telephone Interview for Cognitive Status (TICS): Reliability and validity in a stroke sample. International Journal of Geriatric Psychiatry 1994; 9: 803-7.

Eady et al., Variation in gene expression profiles of peripheral blood mononuclear cells from healthy volunteers. Physiological genomics 2005; 22: 402-11.

Ferrari et al.,Burden of depressive disorders by country, sex, age, and year: findings from the global burden of disease study 2010. PLoS Med 2013; 10: e1001547.

Gaiteri et al., Beyond modules and hubs: the potential of gene coexpression networks for investigating molecular mechanisms of complex brain disorders. Genes, brain, and behavior 2014; 13: 13-24.

Guatelli et al., Isothermal, in vitro amplification of nucleic acids by a multienzyme reaction modeled after retroviral replication, Proc. Natl. Acad. Sci. USA 1990; 87: 1874-1878.

Gunther et al., Prediction of clinical drug efficacy by classification of drug-induced genomic expression profiles in vitro. Proceedings of the National Academy of Sciences of the United States of America 2003; 100: 9608-13.

Hamilton, A rating scale for depression. Journal of Neurology, Neurosurgery, and Psychiatry 1960; 23: 56-62.

Hardeveld et al., Prevalence and predictors of recurrence of major depressive disorder in the adult population. Acta psychiatrica Scandinavica 2010; 122: 184-91.

Hidaka, Depression as a disease of modernity: explanations for increasing prevalence. J Affect Disord 2012; 140: 205-14.

Huerta-Ramirez et al., Diagnosis delay in first episodes of major depression: a study of primary care patients in Spain. J Affect Disord 2013; 150: 1247-50.

Kessler et al., Lifetime prevalence and age-of-onset distributions of DSM-IV disorders in the National Comorbidity Survey Replication. Arch Gen Psychiatry 2005; 62: 593-602.

Kurian et al., Identification of blood biomarkers for psychosis using convergent functional genomics. Molecular psychiatry 2011; 16: 37-58.

Kwoh et al., Transcription-based amplification system and detection of amplified human immunodeficiency virus type 1 with a bead-based sandwich hybridization format, Proc. Natl. Acad. Sci. USA1989; 86:1173-1177.

Le-Niculescu et al., Identifying blood biomarkers for mood disorders using convergent functional genomics. Molecular psychiatry 2009; 14: 156-74.

Lepine et al., he increasing burden of depression. Neuropsychiatr Dis Treat 2011; 7: 3-7.

Leuchter et al., Comparative effectiveness of biomarkers and clinical indicators for predicting outcomes of SSRI treatment in Major Depressive Disorder: results of the BRITE-MD study. Psychiatry Res 2009; 169: 124-31.

Licino et al., Launching the 'war on mental illness'. Molecular psychiatry 2014; 19: 1-5.

Licino et al., Pharmacogenomics of antidepressant treatment effects. Dialogues Clin Neurosci 2011; 13: 63-71.

Liew et al., The peripheral blood transcriptome dynamically reflects system wide biology: a potential diagnostic tool. J Lab Clin Med 2006; 147: 126-32.

Liotti et al., Unmasking disease-specific cerebral blood flow abnormalities: mood challenge in patients with remitted unipolar depression. Am J Psychiatry 2002; 159: 1830-40.

Lizardi et al., Exponential Amplification of Recombinant—RNA Hybridization Probes, Nature BioTechnol. 1988; 6: 1197-1202.

MacArthur Foundation's Initiative on Depression and Primary Care. The MacArthur Initiative on Depression and Primary Care at Dartmouth and Duke: Depression Management Toolkit. Hanover, NH: Dartmouth; 2004, 44 pages.

MaClean et al., Application of 'next-generation' sequencing technologies to microbial genetics, Nature Rev. Microbiol. 2009, 7: 287-296.

The Mammalian Gene Collection, https://genecollections.nci.nih.gov/MGC/, last updated Mar. 2009, retrieved May 1, 2017, 2 pages.

Margulies et al.,Genome sequencing in microfabricated high-density picolitre reactors, Nature. 2005; 437(7057):376-80.

Mehta et al., Gene expression studies in major depression. Curr Psychiatry Rep 2010; 12: 135-44.

Menke et al., Dexamethasone stimulated gene expression in peripheral blood is a sensitive marker for glucocorticoid receptor resistance in depressed patients. Neuropsychopharmacology : official publication of the American College of Neuropsychopharmacology 2012; 37: 1455-64.

Menke, Gene expression: biomarker of antidepressant therapy? Int Rev Psychiatry 2013; 25: 579-91.

Mitra et al., Fluorescent in situ sequencing on polymerase colonies, 2003, Anal Biochem. Sep. 1, 2003;320(1):55-65.

Mohr et al. Effect of telephone-administered vs face-to-face cognitive behavioral therapy on adherence to therapy and depression outcomes among primary care patients: a randomized trial. JAMA, 2012; 307: 2278-85.

Mohr et al., The effect of telephone-administered psychotherapy on depression and attrition: A meta-analysis. Clin Psych Sci & Pract 2008; 15:143-253.

Mohr et al., The peripheral-blood transcriptome: new insights into disease and risk assessment. Trends in Molecular Medicine 2007; 13: 422-32.

(56) References Cited

OTHER PUBLICATIONS

Nelson et al., Detection of Acridinium Esters by Chemiluminescence, Nonisotopic Probing, Blotting, and Sequencing, ch. 17, Larry J. Kricka ed., 2d ed., 1995, pp. 391-428.
Padmos et al., A discriminating messenger RNA signature for bipolar disorder formed by an aberrant expression of inflammatory genes in monocytes. Arch Gen Psychiatry 2008; 65: 395-407.
Pajer et al., Discovery of blood transcriptomic markers for depression in animal models and pilot validation in subjects with early-onset major depression. Transl Psychiatry 2012; 2: e101.
Papakostas et al., Assessment of a multi-assay, serum-based biological diagnostic test for major depressive disorder: a pilot and replication study. Molecular psychiatry 2013; 18: 332-9.
Pence et al., The depression treatment cascade in primary care: a public health perspective. Curr Psychiatry Rep 2012; 14: 328-35.
Pepe et al., Estimation and Comparison of Receiver Operating Characteristic Curves. Stata J 2009; 9: 1.
Persing, "In Vitro Nucleic Acid Amplification Techniques" in Diagnostic Medical Microbiology: Principles and Applications (Persing et al., Eds.), pp. 51-87 (American Society for Microbiology, Washington, DC (1993).
Radich et al., Individual-specific variation of gene expression in peripheral blood leukocytes. Genomics 2004; 83: 980-8.
Riedel et al., Response and remission criteria in major depression—a validation of current practice. J Psychiatr Res 2010; 44: 1063-8.
Rollins et al., Analysis of whole genome biomarker expression in blood and brain. Am J Med Genet B Neuropsychiatr Genet 2010; 153B: 919-36.
Rubin et al., Overexpression, amplification, and androgen regulation of TPD52 in prostate cancer, Cancer Res. 2004;64(11):3814-22.
Segal et al., Antidepressant monotherapy vs sequential pharmacotherapy and mindfulness-based cognitive therapy, or placebo, for relapse prophylaxis in recurrent depression. Arch Gen Psychiatry 2010; 67: 1256-64.
Segman et al., Blood mononuclear cell gene expression signature of postpartum depression. Molecular psychiatry 2010; 15: 93-100, 2.
Sheehan et al., The Mini-International Neuropsychiatric Interview (M.I.N.I.): the development and validation of a structured diagnostic psychiatric interview for DSM-IV and ICD-10. J Clin Psychiatry 1998; 59 Suppl 20: 22-33;quiz 4-57.
Shendure et al., Accurate multiplex polony sequencing of an evolved bacterial genome, Science. 2005; 309(5741):1728-32.
Shyn et al., Novel loci for major depression identified by genome-wide association study of Sequenced Treatment Alternatives to Relieve Depression and meta-analysis of three studies. Molecular psychiatry 2011; 16: 202-15.
Spijker et al., Stimulated gene expression profiles as a blood marker of major depressive disorder. Biological psychiatry 2010; 68: 179-86.
Storey et al., Statistical significance for genomewide studies. Proceedings of the National Academy of Sciences 2003; 100: 9440-5.
Sullivan et al., Evaluating the comparability of gene expression in blood and brain. Am J Med Genet B Neuropsychiatr Genet 2006; 141B: 261-8.
Ten Doesschate et al.,Prediction of recurrence in recurrent depression: a 5.5-year prospective study. J Clin Psychiatry 2010; 71: 984-91.
Voelkerding et al., Next-generation sequencing: from basic research to diagnostics, Clin Chem. Apr. 2009;55(4):641-58.
Walker et al., Isothermal in vitro amplification of DNA by a restriction enzyme/DNA polymerase system, Proc Natl Acad Sci U S A. Jan. 1, 1992;89(1):392-6.
Weiss, Hot prospect for new gene amplifier, Science. Nov. 29, 1991;254(5036):1292-3.
Wray et al., Genome-wide association study of major depressive disorder: new results, meta-analysis, and lessons learned. Molecular psychiatry 2012; 17: 36-48.

* cited by examiner

BIOMARKERS PREDICTIVE OF PREDISPOSITION TO DEPRESSION AND RESPONSE TO TREATMENT

The present application is a continuation-in-part of U.S. patent application Ser. No. 14/598,970, filed Jan. 16, 2015, which claims priority to U.S. Provisional Patent Application No. 61/928,723, filed Jan. 17, 2014, each of which is incorporated by reference in its entirety.

The present application is also a continuation-in-part of U.S. patent application Ser. No. 15/296,807, filed Oct. 18, 2016, which is a continuation of U.S. patent application Ser. No. 14/994,802, filed Jan. 13, 2016, now U.S. Pat. No. 9,469,875, which is a divisional of U.S. patent application Ser. No. 13/276,565, filed Oct. 19, 2011, which claims the priority benefit of U.S. Provisional Patent Application No. 61/394,449, filed Oct. 19, 2010, each of which is incorporated by reference in its entirety.

FIELD

The present invention relates generally to the identification of subjects with a predisposition to recurrent depression, predicting a subject's responsiveness to therapy, and determining whether a subject has remitted from depression following therapy. In particular, provided herein are biomarkers, methods, and kits for such uses.

BACKGROUND

Recurrent and chronic forms of depression account for the bulk of the high burden associated with depression disorders. However, the field is presently unable to predict which individuals, after experiencing a first episode of depression, will go on to have a recurrent or chronic clinical course.

Patient responses to current depression therapies vary significantly, with approximately 60% not remitting (not recovering from depression) after the first treatment choice. Currently there are no tools that can identify prior to treatment whether a patient with depression will respond to a certain type of treatment or not.

SUMMARY

The present invention relates generally to the identification of subjects with a predisposition to recurrent depression, predicting a subject's responsiveness to therapy, and determining whether a subject has remitted from depression following therapy. In particular, provided herein are biomarkers, methods, and kits for such uses.

In some embodiments, the present invention provides methods of assessing depression in a subject, comprising: (a) detecting (e.g., using reagents and analytical techniques described herein), in a sample obtained from the subject, the levels of expression products for a panel of multiple biomarkers, said biomarkers indicative of: (i) vulnerability to recurrent depression, (ii) predicting responsiveness to psychotherapy, and/or (iii) remission following psychotherapy.

In some embodiments, the present invention provides a method for characterizing the risk of future depressive episodes by detecting (e.g., using reagents and analytical techniques described herein), in a sample obtained from the subject, the levels of expression products for a panel of multiple biomarkers, said biomarkers indicative of vulnerability to recurrent depression. In some embodiments, a subject is diagnosed as being vulnerable to (or at risk of) future depressive episodes (e.g., recurring depressive episodes). In some embodiments, methods further comprise taking one or more intervention steps to treat or prevent potential future depressive episodes (e.g., recurring depressive episodes). In some embodiments, methods further comprise subsequent re-testing for said biomarkers indicative of vulnerability to recurrent depression (e.g., after treatment, after a particular time period (e.g., 1 week, 1 month, 6 months, 1 year, 2 years, etc.), etc.).

In some embodiments, the present invention provides a method for predicting responsiveness to psychotherapy by detecting (e.g., using reagents and analytical techniques described herein), in a sample obtained from the subject prior to psychotherapy, the levels of expression products for a panel of multiple biomarkers, said biomarkers indicative of responsiveness to psychotherapy. In some embodiments, a subject is diagnosed as either being responsive nonresponsive to psychotherapy (e.g., yet to be performed psychotherapy). In some embodiments, methods further comprise taking one or more intervention steps to treat or prevent depressive episodes (e.g., psychotherapy for subject determined to be responsive, non-psychotherapy treatment (e.g., pharmaceutical treatment, hospitalization or residential treatment, electroconvulsive therapy (ECT), transcranial magnetic stimulation (TMS), etc.) for subjects determined to be nonresponsive, etc.), etc.).

In some embodiments, the present invention provides a method for objectively determining the success of psychotherapy by detecting (e.g., using reagents and analytical techniques described herein), in a sample obtained from the subject, the levels of expression products for a panel of multiple biomarkers, said biomarkers indicative of remission after psychotherapy. In some embodiments, a subject is diagnosed as being in remission or not in remission (e.g., relapse). In some embodiments, methods further comprise taking one or more intervention steps to treat or depressive episodes. For example, when biomarkers indicate that subject is not in remission, further psychotherapy or a different treatment (e.g., pharmaceutical treatment, hospitalization or residential treatment, electroconvulsive therapy (ECT), transcranial magnetic stimulation (TMS), etc.) is indicated or prescribed. In some embodiments, methods further comprise subsequent re-testing for said biomarkers indicative of remission following psychotherapy (e.g., after treatment additional treatment, after a particular time period (e.g., 1 week, 1 month, 6 months, 1 year, 2 years, etc.), etc.).

In some embodiments, the subject has suffered from depression. In some embodiments, the subject presently suffers from depression or is experiencing a depressive episode. In some embodiments, the human subject is a candidate for psychotherapy. In some embodiments, the panel of multiple biomarkers comprises biomarkers indicative of vulnerability to recurrent depression. In some embodiments, the panel of multiple biomarkers comprises one or more (e.g., 1, 2, or 3) of DGKA, KIAA1539, and RAPH1. In some embodiments, the panel of multiple biomarkers comprises biomarkers predicting responsiveness to psychotherapy. In some embodiments, the panel of multiple biomarkers comprises one or more (e.g., 1, 2, 3, 4, 5, or ranges therein) of RAPH1, PSME1, IGSF4A, ADCY3, FAM46A and DGKA.

In some embodiments, the human subject has completed or is receiving psychotherapy. In some embodiments, the panel of multiple biomarkers comprises biomarkers indicative of remission following psychotherapy. In some embodiments, the panel of multiple biomarkers comprises one or more (e.g., 1, 2, 3, 4, 5, 6, 7, 8, 9, 10, 11, 12, 13, 14, 15, 16, or ranges therein) of RAPH1, DRD2, OSBPL2, DAG1, OTX2, DPPA3, RAB27B, CTTNBP2, LIX1, NTRK2, SLC24A4, MARCKS, ASAH1, ATP11C, KIAA1539, and PSME1. In some embodiments, the panel of multiple biomarkers comprises one or more (e.g., 1, 2, 3, 4, 5, or ranges therein) MARCKS, ASAH1, ATPC11C, KIAA1539, and PSME1.

In some embodiments, expression products are mRNAs corresponding to the biomarkers of the panel. In some embodiments, detecting the levels of expression products comprises exposing the sample to nucleic acid probes complementary to the mRNAs corresponding to the biomarkers of the panel. In some embodiments, nucleic acid probes are covalently linked to a solid surface. In some embodiments, detecting the levels of expression products comprises use of a detection technique selected from the group consisting of microarray analysis, reverse transcriptase PCR, quantitative reverse transcriptase PCR, digital PCR and hybridization analysis.

In some embodiments, detection of expression products comprises generation of cDNA (e.g., by reverse transcription) from the mRNA (e.g., biomarker mRNA) in a sample, and detecting the cDNA. In some embodiments, cDNA is further amplified prior to detection (e.g., by qPCR). In some embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA may be detected or used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

In some embodiments, expression products are proteins corresponding to the biomarkers of the panel. In some embodiments, detecting the levels of expression products comprises exposing the sample to antibodies (or antibody fragments, or aptamers, etc.) for the proteins corresponding to the biomarkers of the panel. In some embodiments, antibodies are covalently linked to a solid surface. In some embodiments, detecting the levels of expression products comprises exposing the sample to a mass analysis technique (e.g., mass spectrometry).

In some embodiments, the present invention provides kits, reagent mixtures, or surfaces comprising reagents for detecting a panel comprising multiple biomarkers, said biomarkers indicative of: (a) vulnerability to recurrent depression, (b) responsiveness to psychotherapy, and/or (c) remission following psychotherapy.

In some embodiments, reagents are provided for the detection and/or quantification of biomarker proteins. Suitable reagents include primary antibodies (e.g., that bind to the biomarkers), secondary antibodies (e.g., that bind primary antibodies), antibody fragments, aptamers, etc. Protein detection reagents may be labeled (e.g., fluorescently) or unlabeled, and may by free in solution or immobilized.

In some embodiments, reagents are provided for the detection and/or quantification of biomarker RNA (e.g., mRNA). Suitable reagents include amplification and/or detection reagents, such as primers and/or probes. Primers and probes may be labeled (e.g., fluorescently) or unlabeled, and may by free in solution or immobilized.

In some embodiments, a kit, reagent mixture, or surface comprises reagents for detecting a panel of multiple biomarkers indicative of vulnerability to recurrent depression. In some embodiments, reagents are for detecting one or more (e.g., 1, 2, 3, or ranges therein) of DGKA, KIAA1539, and RAPH1.

In some embodiments, a kit, reagent mixture, or surface comprises reagents for detecting a panel of multiple biomarkers predicting responsiveness to psychotherapy. In some embodiments, reagents are for detecting one or more (1, 2, 3, 4, 5, or ranges therein) of RAPH1, PSME1, IGSF4A, ADCY3, FAM46A and DGKA.

In some embodiments, a kit, reagent mixture, or surface comprises reagents for detecting a panel of multiple biomarkers measuring remission following psychotherapy. In some embodiments, reagents are for detecting one or more (1, 2, 3, 4, 5, 6, 7, 8, 9, 10, 11, 12, 13, 14, 15, 16, or ranges therein) of RAPH1, DRD2, OSBPL2, DAG1, OTX2, DPPA3, RAB27B, CTTNBP2, LIX1, NTRK2, SLC24A4, MARCKS, ASAH1, ATP11C, KIAA1539, and PSME1. In some embodiments, reagents are for detecting one or more of MARCKS, ASAH1, ATP11C, KIAA1539, and PSME1.

In some embodiments, a panel of depression biomarkers is part of a larger panel of biomarkers (e.g., a panel that also screens for other diseases or conditions (e.g., PTSD, anxiety, etc.). In some embodiments, the depression panel is part of a larger general panel of biomarkers, wherein the general panel comprises or consists of 10,000 or fewer biomarkers (e.g., <5,000 biomarkers, <1,000 biomarkers, <500 biomarkers, <200 biomarkers, <100 biomarker, <50 biomarkers, etc.). In some embodiments, reagents are provided for detection of 4 or more biomarkers selected from RAPH1, DRD2, OSBPL2, DAG1, OTX2, DPPA3, RAB27B, CTTNBP2, LIX1, NTRK2, SLC24A4, MARCKS, ASAH1, ATP11C, KIAA1539, PSME1, ADCY3, IGSF4A, and DGKA (e.g., the selected biomarkers only, among a larger set of depression biomarkers, among a larger set of biomarkers directed to a multiple conditions).

In some embodiments, the present invention provides kits, reagent mixtures, and/or surfaces comprising (or displaying) reagents for detecting a panel of depression biomarkers including one or more biomarkers described herein. In some embodiments, reagents are provided for detection of 100 or fewer depression biomarkers (e.g., <100 biomarkers, <50 biomarkers, <40 biomarkers, <30 biomarkers, <20 biomarkers, <10 biomarkers). In some embodiments, reagents are provided for detection of two of more depression biomarkers (e.g., >3 biomarkers, >4 biomarkers, >5 biomarkers, >6 biomarkers, >7 biomarkers, >8 biomarkers, >9 biomarkers, >10 biomarkers, >15 biomarkers, >20 biomarkers, >30 biomarkers, >40 biomarkers). In some embodiments, the depression characterizing reagents are provided with reagents for detection of other non-depression biomarkers (e.g., biomarkers that for other diseases or conditions (e.g., PTSD, anxiety, etc.)). In some embodiments, reagents are proved for detecting less than 10,000 depression biomarkers and non-depression biomarkers combined (e.g., <5,000 biomarkers, <1,000 biomarkers, <500 biomarkers, <200 biomarkers, <100 biomarker, <50 biomarkers, etc.).

In some embodiments, the present invention provides methods for characterizing depression in a subject, comprising detecting, in a sample obtained from the subject, the levels of expression products for a panel of biomarkers, said biomarkers indicative of two or more of: (a) vulnerability to recurrent depression, (b) predicting responsiveness to psychotherapy, and (c) determining remission following psychotherapy.

In some embodiments, the present invention provides methods for characterizing a sample as having been obtained from a human subject who is: (i) vulnerable to recurrent depression, (ii) predict if the subject will be responsive or non-responsive to psychotherapy for treatment of depression, and/or (iii) objectively measure remission following psychotherapy for depression, said method comprising one or more of the steps of: (a) receiving a sample obtained from the subject; (b) detecting in the sample the level a panel of biomarkers selected from biomarkers indicative of: (i) vulnerability to recurrent depression, (ii) responsiveness to psychotherapy, and/or (iii) remission following psychotherapy; (c) using a computer-based analysis program is used to convert the data generated in steps (b) into a depression assessment for the human subject from which the sample was obtained; and (d) generating a report describing the depression assessment of step (c).

In some embodiments, the present invention provides methods of testing a subject for (i) vulnerability to recurrent depression, (ii) responsiveness or non-responsiveness to psychotherapy for treatment of depression, and/or (iii) remission following psychotherapy for depression, said method comprising: (a) obtaining a sample from the subject; (b) providing the sample to testing facility to be tested for levels expression products corresponding to a panel of multiple biomarkers indicative of: (i) vulnerability to recurrent depression, (ii) responsiveness to psychotherapy, and (iii) remission following psychotherapy; and (c) receiving a report from the testing facility, said report including a depression assessment of said subject.

In some embodiments, methods further comprise determining a treatment course of action for said subject. In some embodiments, a treatment course of action comprises psychotherapy. In some embodiments, a treatment course of action comprises cognitive behavior therapy. In some embodiments, methods further comprise administering treatment (e.g., psychotherapy (e.g., cognitive behavior therapy, etc.), etc.) to a subject (e.g., based on characteristics of subject's depression determined using biomarkers described herein).

In some embodiments, provided herein are methods of treating depression in a subject comprising (a) determining the levels of one or more biomarkers described herein in a biological sample from a subject, said biomarkers being indicative or diagnostic of (i) vulnerability to recurrent depression, (ii) responsiveness or non-responsiveness to psychotherapy for treatment of depression, and/or (iii) remission following psychotherapy for depression, and (b) administering a therapy for depression. In some embodiments, therapy is selected from the group consisting of psychoanalysis, psychotherapy, pharmaceutical treatment, electroshock therapy, etc.

In some embodiments, biomarkers indicative or diagnostic of (i) vulnerability to recurrent depression, (ii) responsiveness or non-responsiveness to psychotherapy for treatment of depression, and/or (iii) remission following psychotherapy for depression are proteins or protein subunits, the concentration of which in a biological sample (e.g., blood, urine, tissues, etc.) are altered when compared to a control. In some embodiments, protein detection and/or quantification reagents are provided. In embodiments in which a biomarker is a protein, polypeptide and/or peptide, detection and/or quantification reagents may comprise antibodies or antibody-like reagents, aptamers, etc. that bind (e.g., specifically) to the biomarker(s). In such embodiments, detection and/or quantification may be achieved by, for example, an immunoassay, Western blot, enzyme-linked immunosorbent assay (ELISA), radioimmunoassay (RIA), fluorimetric assay, or other suitable assays known in the field.

In some embodiments, biomarkers indicative or diagnostic of (i) vulnerability to recurrent depression, (ii) responsiveness or non-responsiveness to psychotherapy for treatment of depression, and/or (iii) remission following psychotherapy for depression are RNAs (e.g., mRNA) encoding proteins or subunits thereof, the concentration or level of expression of which (e.g., in a biological sample (e.g., blood, urine, tissues, etc.)) are altered when compared to a control. In embodiments in which a biomarker is an RNA (e.g., mRNA), detection and/or quantification reagents may comprise primers (e.g., for amplification, reverse transcription, etc.) or probes (e.g., detectably-labeled (e.g., optically-labeled, fluorescently labeled, etc.) oligonucleotides) that bind (e.g., specifically) to the biomarker. In such embodiments, detection and/or quantification may be achieved by, for example, RT-PCR, qPCR, Northern blot analysis, an enzymatic cleavage assay (e.g., INVADER, Hologic, Inc.; See e.g., U.S. Pat. Nos. 5,846,717, 6,090,543; 6,001,567; 5,985,557; and 5,994,069; each of which is herein incorporated by reference), a hybridization assay (e.g., TaqMan assay (Life Technologies; See e.g., U.S. Pat. Nos. 5,962,233 and 5,538,848, each of which is herein incorporated by reference), etc.

Definitions

As used herein, the term "subject" broadly refers to any animal, including but not limited to, human and non-human animals (e.g., dogs, cats, cows, horses, sheep, poultry, fish, crustaceans, etc.). As used herein, the term "patient" typically refers to a subject that is being treated for a disease or condition.

As used herein, the term "sample" is used in its broadest sense. In one sense it can refer to biological samples obtained from animals (including humans) and encompass fluids, solids, tissues (e.g., neurological tissue), and gases. Biological samples include blood products (e.g., plasma and serum), saliva, urine, and the like. These examples are not to be construed as limiting the sample types applicable to the present invention.

As used here, the term "antibody" includes monoclonal antibodies (including full length monoclonal antibodies), polyclonal antibodies, multispecific antibodies (e.g., bispecific antibodies), humanized antibodies, and antibody fragments so long as they exhibit the desired biological activity. Antibodies can be conjugated to other molecules (e.g., toxins). As used herein, the term "antibody fragments" refers to a portion of an intact antibody. Examples of antibody fragments include, but are not limited to, linear antibodies; single-chain antibody molecules; Fc or Fc' peptides, Fab and Fab fragments, and multispecific antibodies formed from antibody fragments.

The terms "specific binding" or "specifically binding" when used in reference to the interaction of capture or detection reagent (e.g., antibody probe etc.) and a target or biomarker (e.g., protein, DNA, RNA, etc.) means that the interaction is dependent upon the presence of a particular structure (i.e., the antigenic determinant or epitope; the nucleic acid sequence).

As used herein, the terms "non-specific binding" and "background binding" when used in reference to the interaction capture or detection reagent (e.g., antibody probe etc.) and a target or biomarker (e.g., protein, DNA, RNA, etc.)

refer to an interaction that is not dependent on the presence of a particular structure or sequence.

As used herein, "a reagent that specifically detects expression levels" refers to reagents used to detect the expression of one or more genes (e.g., including but not limited to, the biomarkers herein). Examples of suitable reagents include but are not limited to, nucleic acid probes capable of specifically hybridizing to the gene of interest, aptamers, PCR primers capable of specifically amplifying the gene of interest, and antibodies capable of specifically binding to proteins expressed by the gene of interest.

As used herein, the term "nucleic acid detection assay" refers to any method of determining the nucleotide composition of a nucleic acid of interest. Nucleic acid detection assay include but are not limited to, DNA sequencing methods, probe hybridization methods, enzyme mismatch cleavage methods (e.g., Variagenics, U.S. Pat. Nos. 6,110,684, 5,958,692, 5,851,770, herein incorporated by reference in their entireties); polymerase chain reaction; branched hybridization methods (e.g., Chiron, U.S. Pat. Nos. 5,849,481, 5,710,264, 5,124,246, and 5,624,802, herein incorporated by reference in their entireties); rolling circle replication (e.g., U.S. Pat. Nos. 6,210,884, 6,183,960 and 6,235,502, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (e.g., Barnay Proc. Natl. Acad. Sci USA 88, 189-93 (1991)); and sandwich hybridization methods (e.g., U.S. Pat. No. 5,288,609, herein incorporated by reference in its entirety).

The term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (e.g., in the presence of nucleotides and an inducing agent such as a DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, and the use of the method.

The term "probe" refers to an oligonucleotide (e.g., a sequence of nucleotides), whether occurring naturally as in a purified restriction digest or produced synthetically, recombinantly, or by PCR amplification, that is capable of hybridizing to another oligonucleotide of interest. A probe may be single-stranded or double-stranded. Probes are useful in the detection, identification, and isolation of particular gene sequences (e.g., a "capture probe"). It is contemplated that any probe used in the present invention may, in some embodiments, be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, a "diagnostic" test application includes the detection or identification of a disease state or condition of a subject, determining the likelihood that a subject will contract a given disease or condition, determining the likelihood that a subject with a disease or condition will respond to therapy, determining the prognosis of a subject with a disease or condition (or its likely progression or regression), and determining the effect of a treatment on a subject with a disease or condition.

DETAILED DESCRIPTION

The present invention relates generally to the identification of subjects with a predisposition to recurrent depression, predicting a subject's responsiveness to therapy, and determining whether a subject has remitted from depression following therapy. In particular, provided herein are biomarkers, methods, and kits for such uses.

In some embodiments, the present invention provides biomarkers useful when assessing a new patient, prior to determining a treatment course (e.g., psychotherapy, pharmaceuticals, etc.), and following a course of treatment. In some embodiments, the biomarkers herein (e.g., vulnerability biomarkers, responsiveness biomarkers, and remission biomarkers) are useful in assessing a patient, determining a treatment course, and/or assessing the success of a treatment.

Provided herein are biomarkers useful in characterizing depression (e.g., recurrent depression) in a subject. In certain embodiments, biomarkers provided herein find use in one or more of: (I) predicting a subject's vulnerability to recurrent depression (e.g., diagnosing a subject as being at-risk for recurrent depression), (II) predicting a subject's responsiveness to therapy (e.g., psychotherapy (e.g., CBT)), and (III) remission in a subject following treatment. In some embodiments, detecting such biomarkers informs and/or determines a treatment course of action for the subject.

I. Biomarkers Predictive of Vulnerability to Recurrent Depression

In some embodiments, the present invention provides biomarkers (e.g., DGKA, KIAA1539, RAPH1, etc.) that are predictive of vulnerability to recurrent depression. In some embodiments, gene expression levels and/or concentration (e.g., of mRNA, of protein) in the body (e.g., in urine, in blood, etc.) of vulnerability biomarkers are significantly altered for subjects at risk of recurrent depression. In some embodiments, biomarkers are altered in at-risk subjects whether or not they are currently experiencing a depressive episode. In some embodiments, subjects not at risk for recurrent depression exhibit normal biomarker levels whether or not they are currently experiencing a depressive episode.

In certain embodiments, the present invention provides a panel of biomarkers (e.g., blood biomarkers (e.g., genes that are over or under expressed), etc.) that indicate vulnerability to recurrent depression. In some embodiments, subjects vulnerable to recurrent depression exhibit distinct expression pattern and/or biomarker levels in comparison control group. In some embodiments, subjects vulnerable to recurrent depression exhibit expression patterns and/or biomarker levels beyond a threshold value.

In some embodiments, the present invention provides biological markers indicative of a vulnerability to recurrent depression in a subject. In some embodiments, the presence of such biomarkers (e.g., elevated or reduced expression of biomarker genes) is indicative of and/or diagnostic of vulnerability to recurrent depression. In some embodiments, biological markers are blood biomarkers. In some embodiments, the present invention provides one or more biomarkers, or a panel of biological markers, that can be identified from tissue or blood or other sample types. In some embodiments, these biological markers show increased or decreased levels of gene-specific RNA in subjects with vulnerable to recurrent depression compared to those of controls (e.g., a subject who has experienced depression but is not vulnerable to recurrent depression, a subject currently experiencing depression but not vulnerable to recurrent depression, a subject not vulnerable to depression, etc.). In some embodiments, these biological markers show increased or decreased levels of protein expressed from these genes in subjects vulnerable to recurrent depression compared to those of controls (e.g., a subject not vulnerable to recurrent depression, etc.).

In some embodiments, a subject to be tested by the methods and reagents described herein exhibits one or more symptoms of depression and/or has one or more risk factors for depression. Symptoms of depression include, for example: feelings of sadness, emptiness or unhappiness; angry outbursts, irritability or frustration, even over small matters; loss of interest or pleasure in normal activities, such as sex; sleep disturbances, including insomnia or sleeping too much; tiredness and lack of energy, so that even small tasks take extra effort; changes in appetite—often reduced appetite and weight loss, but increased cravings for food and weight gain in some people; anxiety, agitation or restlessness—for example, excessive worrying, pacing, hand-wringing or an inability to sit still; slowed thinking, speaking or body movements; feelings of worthlessness or guilt, fixating on past failures or blaming yourself for things that are not your responsibility; trouble thinking, concentrating, making decisions and remembering things; frequent thoughts of death, suicidal thoughts, suicide attempts or suicide; Unexplained physical problems, such as back pain or headaches; etc. Risk factors of depression include, for example: depression that started when you were a teen or child; history of anxiety disorder, borderline personality disorder or post-traumatic stress disorder; abuse of alcohol or illegal drugs; certain personality traits, such as having low self-esteem and being overly dependent, self-critical or pessimistic; serious or chronic illness, such as cancer, diabetes or heart disease; certain medications, such as some high blood pressure medications or sleeping pills (talk to your doctor before stopping any medication); traumatic or stressful events, such as physical or sexual abuse, the loss of a loved one, a difficult relationship or financial problems; blood relatives with a history of depression, bipolar disorder, alcoholism or suicide; etc. In some embodiments, prior to, concurrent with, and/or following testing a subject for the biomarkers of vulnerability to recurrent depression described herein, a subject is evaluated for symptoms and/or risk factors.

In some embodiments, biomarkers provide confirmation that a subject's depression is at least partially the result of vulnerability to recurrent depression. In other embodiments, biomarkers predict whether a subject who has depression in the past is likely to have depressive episodes at a later time. In some embodiments, biomarkers allow diagnosis of vulnerability to recurrent depression in a subject not actively experiencing symptoms or unable to communicate such symptoms. In some embodiments, biomarkers differentiate between a subject experiencing symptoms caused by a single depression-causing event and those related to vulnerability to recurrent depression.

In certain embodiments, the present invention relates to the vulnerability biomarkers and/or the use thereof in detecting, characterizing, identifying, and/or diagnosing vulnerability to recurrent depression in a subject. Experiments were conducted during development of embodiments of the present invention to identify biomarkers that are indicative and/or diagnostic of vulnerability to recurrent depression. In some embodiments, the present invention provides a panel of biomarkers comprising a plurality (e.g., 2, 3, 4, 5, 6, 7, 8, 9, 10 . . . 15 . . . 20 . . . 30 . . . 40, or more) of vulnerability biomarkers (e.g., DGKA, KIAA1539, RAPH1, etc.). In some embodiments the present invention provides reagents for detecting genes or encoded proteins comprising one or more genes (e.g., DGKA, KIAA1539, RAPH1, etc.). In some embodiments, a panel comprises one or more reagents for detecting vulnerability biomarker genes or encoded proteins (e.g., DGKA, KIAA1539, RAPH1, etc.) and one or more additional genes. In some embodiments, the present invention provides a set of genes whose mRNA levels differ in (e.g., in the blood of) subjects showing higher and lower level of vulnerability to recurrent depression. In some embodiments, the present invention provides a set of genes whose protein levels differ in (e.g., in the blood of) subjects showing higher and lower level of vulnerability to recurrent depression. In some embodiments of the present invention, one or more such genes are used to diagnose or suggest vulnerability to recurrent depression from human sample (e.g., blood sample). In some embodiments, the presence of a gene or panel of genes (or altered levels of such genes) that correlates with vulnerability to recurrent depression (e.g., is indicative of vulnerability to recurrent depression, is diagnostic of vulnerability to recurrent depression) allows a treating physician to take any number of courses of action, including, but not limited to, further diagnostic assessment, selection of appropriate treatment (e.g., pharmaceutical, nutritional, counseling, and the like), increased or decreased monitoring, etc. In some embodiments, changes in expression of a gene or panel of genes that correlates with vulnerability to recurrent depression (e.g., is indicative of vulnerability to recurrent depression, is diagnostic of vulnerability to recurrent depression) allows a treating physician to take any number of courses of action, including, but not limited to, further diagnostic assessment, selection of appropriate treatment (e.g., pharmaceutical, nutritional, counseling, and the like), increased or decreased monitoring, etc.

In some embodiments the present invention provides a method for detecting or assessing the risk of recurrent depression in a subject. In some embodiments the present invention provides a method for diagnosing vulnerability to recurrent depression in a subject. In some embodiments, the biomarkers provided herein are used in conjunction with other evidence of vulnerability to recurrent depression (e.g., symptoms, risk factors, etc.) in making a diagnosis. In some embodiments, the biomarkers provided herein are used in the absence of other evidence of vulnerability to recurrent depression (e.g., symptoms, risk factors, etc.) in making a diagnosis.

II. Biomarkers Predictive of Responsiveness to Psychotherapy

In some embodiments, the present invention provides biomarkers (e.g., RAPH1, PSME1, IGSF4A, ADCY3, FAM46A, DGKA, etc.) that are predictive of a subject's responsiveness to psychotherapy (e.g., cognitive behavioral therapy (CBT)). In some embodiments, gene expression levels and/or concentration (e.g., of mRNA, of protein) in the body (e.g., in urine, in blood, etc.) of responsiveness biomarkers are significantly altered in subjects who will be responsive to psychotherapy (e.g., CBT) versus those who will not. In some embodiments, biomarkers are predictive of psychotherapy (e.g., CBT) responsiveness prior to a subject undergoing such therapy. In some embodiments, biomarkers are predictive of psychotherapy (e.g., CBT) responsiveness whether or not a subject is a candidate for such therapy. In some embodiments, biomarkers are predictive of psychotherapy (e.g., CBT) responsiveness whether or not a subject suffers from depression (e.g., recurrent depression) or is presently experiencing depression.

In certain embodiments, the present invention provides a panel of biomarkers (e.g., blood biomarkers (e.g., genes that are over or under expressed), etc.) that indicate responsiveness to psychotherapy (e.g., cognitive behavioral therapy (CBT)). In some embodiments, subjects responsive to treatment by psychotherapy (e.g., cognitive behavioral therapy (CBT)) for depression (e.g., recurrent depression) exhibit distinct expression pattern and/or biomarker levels from subject not responsive to treatment by psychotherapy (e.g., cognitive behavioral therapy (CBT)) for depression (e.g., recurrent depression). In some embodiments, subjects responsive to treatment by psychotherapy (e.g., cognitive behavioral therapy (CBT)) for depression (e.g., recurrent depression) exhibit expression patterns and/or biomarker levels beyond a threshold value. In some embodiments, subjects not responsive to treatment by psychotherapy (e.g., cognitive behavioral therapy (CBT)) for depression (e.g., recurrent depression) exhibit expression patterns and/or biomarker levels beyond a threshold value.

In some embodiments, the present invention provides biological markers indicative of responsiveness/non-responsiveness to treatment by psychotherapy (e.g., cognitive behavioral therapy (CBT)) for depression (e.g., recurrent depression). In some embodiments, the presence of such biomarkers (e.g., elevated or reduced expression of biomarker genes) is indicative of and/or diagnostic of responsiveness/non-responsiveness to treatment by psychotherapy (e.g., cognitive behavioral therapy (CBT)) for depression (e.g., recurrent depression). In some embodiments, biological markers are blood biomarkers. In some embodiments, the present invention provides one or more biomarkers, or a panel of biological markers, that can be identified from tissue or blood or other sample types. In some embodiments, these biological markers show increased or decreased levels of gene-specific RNA in subjects responsive/non-responsive to treatment by psychotherapy (e.g., cognitive behavioral therapy (CBT)) for depression (e.g., recurrent depression) compared to those of controls. In some embodiments, these biological markers show increased or decreased levels of protein expressed from these genes in subjects responsive/non-responsive to treatment by psychotherapy (e.g., cognitive behavioral therapy (CBT)) for depression (e.g., recurrent depression) compared to those of controls.

In some embodiments, a subject to be tested by the methods and reagents described herein exhibits one or more symptoms of depression and/or has one or more risk factors for depression. Symptoms of depression include, for example: feelings of sadness, emptiness or unhappiness; angry outbursts, irritability or frustration, even over small matters; loss of interest or pleasure in normal activities, such as sex; sleep disturbances, including insomnia or sleeping too much; tiredness and lack of energy, so that even small tasks take extra effort; changes in appetite—often reduced appetite and weight loss, but increased cravings for food and weight gain in some people; anxiety, agitation or restlessness—for example, excessive worrying, pacing, hand-wringing or an inability to sit still; slowed thinking, speaking or body movements; feelings of worthlessness or guilt, fixating on past failures or blaming yourself for things that are not your responsibility; trouble thinking, concentrating, making decisions and remembering things; frequent thoughts of death, suicidal thoughts, suicide attempts or suicide; Unexplained physical problems, such as back pain or headaches; etc. Risk factors of depression include, for example: depression that started when you were a teen or child; history of anxiety disorder, borderline personality disorder or post-traumatic stress disorder; abuse of alcohol or illegal drugs; certain personality traits, such as having low self-esteem and being overly dependent, self-critical or pessimistic; serious or chronic illness, such as cancer, diabetes or heart disease; certain medications, such as some high blood pressure medications or sleeping pills (talk to your doctor before stopping any medication); traumatic or stressful events, such as physical or sexual abuse, the loss of a loved one, a difficult relationship or financial problems; blood relatives with a history of depression, bipolar disorder, alcoholism or suicide; etc. In some embodiments, prior to, concurrent with, and/or following testing a subject for the biomarkers of responsiveness/non-responsiveness to treatment by psychotherapy described herein, a subject is evaluated for symptoms and/or risk factors.

In certain embodiments, the present invention relates to the responsiveness biomarkers and/or the use thereof in detecting, characterizing, identifying, and/or diagnosing responsiveness/non-responsiveness to treatment by psychotherapy (e.g., cognitive behavioral therapy (CBT)) for depression (e.g., recurrent depression) in a subject. Experiments were conducted during development of embodiments of the present invention to identify biomarkers that are indicative and/or diagnostic of responsive/non-responsive to treatment by psychotherapy (e.g., cognitive behavioral therapy (CBT)) for depression (e.g., recurrent depression). In some embodiments, the present invention provides a panel of biomarkers comprising a plurality (e.g., 2, 3, 4, 5, 6, 7, 8, 9, 10 . . . 15 . . . 20 . . . 30 . . . 40, or more) of responsiveness biomarkers (e.g., RAPH1, PSME1, IGSF4A, ADCY3, FAM46A, DGKA, etc.). In some embodiments the present invention provides reagents for detecting genes or encoded proteins comprising one or more genes (e.g., RAPH1, PSME1, IGSF4A, ADCY3, FAM46A, DGKA, etc.). In some embodiments, a panel comprises one or more reagents for detecting responsiveness biomarker genes or encoded proteins (e.g., RAPH1, PSME1, IGSF4A, ADCY3, FAM46A, DGKA, etc.) and one or more additional genes. In some embodiments, the present invention provides a set of genes whose mRNA levels differ in (e.g., in the blood of) subjects showing higher and lower level of responsiveness to treatment by psychotherapy (e.g., cognitive behavioral therapy (CBT)) for depression (e.g., recurrent depression). In some embodiments, the present invention provides a set of genes whose protein levels differ in (e.g., in the blood of) subjects showing higher and lower level of responsiveness to treatment by psychotherapy (e.g., cognitive behavioral therapy (CBT)) for depression (e.g., recurrent depression). In some embodiments of the present invention, one or more such genes are used to diagnose or suggest responsiveness/non-responsiveness from human sample (e.g., blood sample) taken prior to treatment. In some embodiments, the presence of a gene or panel of genes (or altered levels of such genes or expression product) that correlates with responsiveness/non-responsiveness to treatment by psychotherapy (e.g., cognitive behavioral therapy (CBT)) for depression (e.g., recurrent depression) allows a treating physician to take any number of courses of action, including, but not limited to, further diagnostic assessment, selection of appropriate treatment (e.g., pharmaceutical, nutritional, counseling, and the like), increased or decreased monitoring, etc. In some embodiments, changes in expression of a gene or panel of genes that correlates with responsiveness/non-responsiveness to treatment by psychotherapy (e.g., cognitive behavioral therapy (CBT)) for depression (e.g., recurrent depression) allows a treating physician to take any number of courses of action, including, but not limited to, further diagnostic assessment, selection of appropriate treatment (e.g., pharmaceutical, nutritional, counseling, and the like), increased or decreased monitoring, increase or decrease in dosage (e.g., of pharmaceutical treatment), increase or decrease in amount of psychoanalysis, etc.

III. Biomarkers Diagnostic/Indicative of Remission Following Treatment

In some embodiments, the present invention provides biomarkers (e.g., RAPH1, DRD2, OSBPL2, DAG1, OTX2, DPPA3, RAB27B, CTTNBP2, LIX1, NTRK2, SLC24A4, MARCKS, ASAH1, ATP11C, KIAA1539, PSME1, etc.) that are indicative and/or diagnostic of whether a subject who has undergone treatment (e.g., psychotherapy (e.g., cognitive behavioral therapy, etc.), etc.) has remitted. In some embodiments, gene expression levels and/or concentration (e.g., of mRNA, of protein) in the body (e.g., in urine, in blood, etc.) of such remission biomarkers are significantly altered in subjects who remitted following therapy (e.g., psychotherapy (e.g., CBT)) versus those who did not. In some embodiments, differences in remission biomarkers are apparent following administration of therapy (e.g., psychotherapy (e.g., CBT)). In some embodiments, remission biomarkers are indicative whether or not the subject is presently experiencing remission or relapse. In some embodiments, remission biomarkers are indicative and/or diagnostic whether or not the subject's belief of remission or relapse at the time of testing is accurate.

In certain embodiments, the present invention provides a panel of biomarkers (e.g., blood biomarkers (e.g., genes that are over or under expressed), etc.) that indicate whether a subject who has undergone treatment (e.g., psychotherapy (e.g., cognitive behavioral therapy, etc.), etc.) remitted or not. In some embodiments, subjects who remitted exhibit distinct expression pattern and/or biomarker levels from subjects who did not. In some embodiments, subjects who remitted exhibit expression patterns and/or biomarker levels beyond a threshold value (e.g., following treatment (e.g., psychotherapy (e.g., cognitive behavioral therapy, etc.), etc.). In some embodiments, subjects who did not remit exhibit expression patterns and/or biomarker levels beyond a threshold value (e.g., following treatment (e.g., psychotherapy (e.g., cognitive behavioral therapy, etc.), etc.).

In some embodiments, the present invention provides biological markers indicative of relapsing/remitting following treatment by psychotherapy (e.g., cognitive behavioral therapy (CBT)) for depression (e.g., recurrent depression). In some embodiments, the presence of such biomarkers (e.g., elevated or reduced expression of biomarker genes) is indicative of and/or diagnostic of relapsing/remitting following treatment by psychotherapy (e.g., cognitive behavioral therapy (CBT)) for depression (e.g., recurrent depression). In some embodiments, biological markers are blood biomarkers. In some embodiments, the present invention provides one or more biomarkers, or a panel of biological markers, that can be identified from tissue or blood or other sample types. In some embodiments, these biological markers show increased or decreased levels of gene-specific RNA in subjects relapsing/remitting following treatment by psychotherapy (e.g., cognitive behavioral therapy (CBT)) for depression (e.g., recurrent depression) compared to those of controls. In some embodiments, these biological markers show increased or decreased levels of protein expressed from these genes in subjects relapsing/remitting following treatment by psychotherapy (e.g., cognitive behavioral therapy (CBT)) for depression (e.g., recurrent depression) compared to those of controls.

In some embodiments, a subject to be tested by the methods and reagents described herein exhibits one or more symptoms of depression and/or has one or more risk factors for depression. Symptoms of depression include, for example: feelings of sadness, emptiness or unhappiness; angry outbursts, irritability or frustration, even over small matters; loss of interest or pleasure in normal activities, such as sex; sleep disturbances, including insomnia or sleeping too much; tiredness and lack of energy, so that even small tasks take extra effort; changes in appetite—often reduced appetite and weight loss, but increased cravings for food and weight gain in some people; anxiety, agitation or restlessness—for example, excessive worrying, pacing, hand-wringing or an inability to sit still; slowed thinking, speaking or body movements; feelings of worthlessness or guilt, fixating on past failures or blaming yourself for things that are not your responsibility; trouble thinking, concentrating, making decisions and remembering things; frequent thoughts of death, suicidal thoughts, suicide attempts or suicide; Unexplained physical problems, such as back pain or headaches; etc. Risk factors of depression include, for example: depression that started when you were a teen or child; history of anxiety disorder, borderline personality disorder or post-traumatic stress disorder; abuse of alcohol or illegal drugs; certain personality traits, such as having low self-esteem and being overly dependent, self-critical or pessimistic; serious or chronic illness, such as cancer, diabetes or heart disease; certain medications, such as some high blood pressure medications or sleeping pills (talk to your doctor before stopping any medication); traumatic or stressful events, such as physical or sexual abuse, the loss of a loved one, a difficult relationship or financial problems; blood relatives with a history of depression, bipolar disorder, alcoholism or suicide; etc. In some embodiments, prior to, concurrent with, and/or following testing a subject for the biomarkers indicative of relapsing/remitting following treatment by psychotherapy described herein, a subject is evaluated for symptoms and/or risk factors.

In certain embodiments, the present invention relates to remission biomarkers and/or the use thereof in detecting, characterizing, identifying, and/or diagnosing relapsing or remitting following treatment by psychotherapy (e.g., cognitive behavioral therapy (CBT)) for depression (e.g., recurrent depression) in a subject. Experiments were conducted during development of embodiments of the present invention to identify biomarkers that are indicative and/or diagnostic of remission following treatment by psychotherapy (e.g., cognitive behavioral therapy (CBT)) for depression (e.g., recurrent depression). In some embodiments, the present invention provides a panel of biomarkers comprising a plurality (e.g., 2, 3, 4, 5, 6, 7, 8, 9, 10 . . . 15 . . . 20 . . . 30 . . . 40, or more) of remission biomarkers (e.g., RAPH1, DRD2, OSBPL2, DAG1, OTX2, DPPA3, RAB27B, CTTNBP2, LIX1, NTRK2, SLC24A4, MARCKS, ASAH1, ATP11C, KIAA1539, PSME1, etc.). In some embodiments the present invention provides reagents for detecting genes or encoded proteins comprising one or more genes (e.g., RAPH1, DRD2, OSBPL2, DAG1, OTX2, DPPA3, RAB27B, CTTNBP2, LIX1, NTRK2, SLC24A4, MARCKS, ASAH1, ATP11C, KIAA1539, PSME1, etc.). In some embodiments, a panel comprises one or more reagents for detecting remission biomarker genes or encoded proteins (e.g., RAPH1, DRD2, OSBPL2, DAG1, OTX2, DPPA3, RAB27B, CTTNBP2, LIX1, NTRK2, SLC24A4, MARCKS, ASAH1, ATP11C, KIAA1539, PSME1, etc.) and one or more additional genes. In some embodiments, the present invention provides a set of genes whose mRNA levels differ in (e.g., in the blood of) subjects showing higher and lower level of remission following treatment by psychotherapy (e.g., cognitive behavioral therapy (CBT)) for depression (e.g., recurrent depression). In some embodiments, the present invention provides a set of genes whose protein levels differ in (e.g., in the blood of) subjects (following treatment) that show higher or lower level of remission. In some embodiments of the present invention, one or more such genes are used to diagnose or suggest of remission/relapse from human sample (e.g., blood sample) taken following treatment. In some embodiments, the presence of a gene or panel of genes (or altered levels of such genes or expression product) that correlates with remission following treatment by psychotherapy (e.g., cognitive behavioral therapy (CBT)) for depression (e.g., recurrent depression) allows a treating physician to take any number of courses of action, including, but not limited to, further diagnostic assessment, selection of appropriate treatment (e.g., pharmaceutical, nutritional, counseling, and the like), increased or decreased monitoring, increase or decrease in dosage (e.g., of pharmaceutical treatment), increase or decrease in amount of psychoanalysis, etc.

IV. Systems, Kits, Reagents, Methods, Uses, Etc.

In some embodiments the present invention provides methods for characterizing the level of gene expression of a panel of genes comprising detecting the amount of mRNA. In some embodiments, the panel comprises 1, 2, 3, 4, 5, 6, 7, 8, 9, 10, 11, 12, 13, 14, 15, 16, 17, 18, 19, 20 . . . 30 . . . 40, or more genes. In some embodiments the present invention provides methods comprising the step of exposing a sample to nucleic acid probes complementary to the mRNA of a panel of genes selected from the genes described herein (e.g., vulnerability biomarkers, responsiveness biomarkers, remission biomarkers, combinations thereof, etc.). In some embodiments the methods employ a nucleic acid detection technique (e.g., microarray analysis, reverse transcriptase PCR, quantitative reverse transcriptase PCR, and hybridization analysis).

In some embodiments the present invention provides methods for characterizing the level of gene expression of a panel of genes by detecting the amount of protein (e.g., in the blood) corresponding to one or more of the genes described herein (e.g., vulnerability biomarkers, responsiveness biomarkers, remission biomarkers, combinations thereof, etc.). In some embodiments the present invention provides methods of detecting changes in the amount of protein (e.g., in the blood) corresponding to one or more of the genes described herein (e.g., vulnerability biomarkers, responsiveness biomarkers, remission biomarkers, combinations thereof, etc.). In some embodiments, a panel comprises 1, 2, 3, 4, 5, 6, 7, 8, 9, 10, 11, 12, 13, 14, 15, 16, 17, 18, 19, 20 . . . 30 . . . 40, etc. genes. In some embodiments the present invention provides methods comprising the step of exposing a sample to antibodies (or antibody fragments, or aptamers, etc.) for the proteins corresponding to one or more of the genes. In some embodiments, detecting a change in the expression of one or more of the genes described herein (e.g., vulnerability biomarkers, responsiveness biomarkers, remission biomarkers, combinations thereof, etc.) comprises exposing a sample (e.g., blood sample) to antibodies (or antibody fragments, or aptamers, etc.) specific to the biomarkers and detecting the binding of the antibodies to the biomarkers.

In some embodiments the present invention relates to gene expression profiles (e.g., increases and/or decrease in the expression of multiple genes) that correlate with vulnerability to recurrent depression, responsiveness to future treatment, and/or remission following treatment, and uses thereof. In some embodiments, a panel of two or more genes is analyzed (e.g., 2 genes . . . 4 genes . . . 6 genes . . . 8 genes . . . 10 genes . . . 15 genes . . . 20 genes . . . 30 genes, or more.). In some embodiments, detection and/or quantification reagents (e.g., oligonucleotide probes) are provided that have specificity for genes described herein (e.g., vulnerability biomarkers, responsiveness biomarkers, remission biomarkers, combinations thereof, etc.).

In some embodiments, the present invention provides a panel of biomarkers for the detection, characterization, and/or diagnosis of a variety of diseases and/or conditions (e.g., psychiatric conditions, mental disease, genetic conditions, physical diseases, etc.), in which the biomarkers described herein are included. In certain embodiments, a panel comprises multiple biomarkers described herein in addition to biomarkers for other diseases or conditions (e.g., PTSD, anxiety, etc.). In particular embodiments, testing a subject (e.g., a blood sample from a subject) for such a panel allows analysis of the depression biomarkers described herein (e.g., vulnerability biomarkers, responsiveness biomarkers, remission biomarkers, combinations thereof, etc.), in addition to biomarkers for other diseases, conditions, or disorders (e.g., PTSD, anxiety, etc.). In some embodiments, all the biomarkers on the panel are provided for a diagnostic or other medical purpose.

In some embodiments, test samples (e.g., containing biomarker protein and/or RNA) are prepared from blood from subjects (e.g., suffering from depression, suspected of suffering from depression, prior to treatment for depression, following treatment for depression, etc.), and the prepared samples are applied to the panel. It is contemplated that the differential hybridization of the patient samples relative to control samples provides an expression signature indicative of depression vulnerability, responsiveness to treatment, remission, etc. In some embodiments, gene expression from a test sample is compared with a prior sample from the same patient to monitor changes over time. In some embodiments, gene expression from a test sample is compared with a sample from the patient under a treatment regimen (e.g., psychoanalytical therapy) to test or monitor the effect of the therapy. In some embodiments, gene expression from a test sample is compared to gene expression from a negative control sample. In some embodiments, gene expression levels from a test sample are compared to predetermined threshold levels identified (e.g., based on population averages for patients with similar age, gender, metabolism, etc.) as "normal." In some embodiments, an increase or decrease of greater than 1.1-fold (e.g., 1.2-fold, 1.5-fold, 2-fold, 3-fold, 5-fold, 10-fold, or higher) compared to "normal" levels or any increase over a normal level or threshold level is indicative of and/or diagnostic. In some embodiments, separate indicative and diagnostic thresholds are established.

The level of biomarker(s) present in a sample may be assessed on an absolute basis or a relative basis. When assessed on a relative basis, comparison may be made to controls including but not limited to a historical sample from the same patient (e.g., serial samples, longitudinal samples); level(s) found in a patient or population of patients absent of disease or disorder; a threshold value; an acceptable range; etc.

In some embodiments, provided herein are DNA-, RNA- and protein-based diagnostic methods that either directly or indirectly detect the biomarkers described herein. The present invention also provides compositions, reagents, and kits for such diagnostic purposes. The diagnostic methods described herein may be qualitative or quantitative. Quantitative diagnostic methods may be used, for example, to compare a detected biomarker level to a cutoff or threshold level. Where applicable, qualitative or quantitative diagnostic methods may also include amplification of target, signal or intermediary.

In some embodiments, biomarkers are detected at the nucleic acid (e.g., RNA) level. For example, the amount of biomarker RNA (e.g., mRNA) present in a sample is determined (e.g., to determine the level of biomarker expression). Biomarker nucleic acid (e.g., RNA, amplified cDNA, etc.) may be detected/quantified using a variety of nucleic acid techniques known to those of ordinary skill in the art, including but not limited to nucleic acid sequencing, nucleic acid hybridization, and nucleic acid amplification.

In some embodiments, a microarray is used. Different kinds of biological assays are called microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is typically a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink-jet printing; or, electrochemistry on microelectrode arrays.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

Genomic DNA and mRNA may be amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. In some embodiments, PCR is digital PCR, see, e.g., Vogelstein, B., & Kinzler, K. W. (1999) "Digital PCR" Proc. Natl. Acad. Sci. USA 96:9236-9241; herein incorporated by reference in its entirety. For other various permutations of PCR see, e.g., U.S. Pat. Nos. 4,683,195, 4,683,202 and 4,800,159; Mullis et al., Meth. Enzymol. 155: 335 (1987); and, Murakawa et al., DNA 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399, 491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., Science 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., Proc. Natl. Acad. Sci. USA 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPαS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., BioTechnol. 6: 1197 (1988), herein incorporated by reference in its entirety), commonly referred to as Qβ replicase; a transcription based amplification method (Kwoh et al., Proc. Natl. Acad. Sci. USA 86:1173 (1989)); and, self-sustained sequence replication (Guatelli et al., Proc. Natl. Acad. Sci. USA 87: 1874 (1990), each of which is herein incorporated by reference in its entirety). For further discussion of known amplification methods see Persing, David H., "In Vitro Nucleic Acid Amplification Techniques" in Diagnostic Medical Microbiology: Principles and Applications (Persing et al., Eds.), pp. 51-87 (American Society for Microbiology, Washington, D.C. (1993)).

Non-amplified or amplified nucleic acids can be detected by any conventional means. For example, in some embodiments, nucleic acids are detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety). Another illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541,205, each of which is herein incorporated by reference in its entirety. Another method for determining the quantity of target sequence initially present in a sample, but which is not based on a real-time amplification, is disclosed in U.S. Pat. No. 5,710,029, herein incorporated by reference in its entirety. Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs are disclosed in U.S. Pat. No. 6,534,274, herein incorporated by reference in its entirety.

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed in U.S. Pat. Nos. 5,925,517 and 6,150,097, herein incorporated by reference in its entirety.

Other self-hybridizing probes are well known to those of ordinary skill in the art. By way of non-limiting example, probe binding pairs having interacting labels, such as those disclosed in U.S. Pat. No. 5,928,862 (herein incorporated by reference in its entirety) might be adapted for use in the present invention. Probe systems used to detect single nucleotide polymorphisms (SNPs) might also be utilized in the present invention. Additional detection systems include "molecular switches," as disclosed in U.S. Publ. No. 20050042638, herein incorporated by reference in its entirety. Other probes, such as those comprising intercalating dyes and/or fluorochromes, are also useful for detection of amplification products in the present invention. See, e.g., U.S. Pat. No. 5,814,447 (herein incorporated by reference in its entirety).

In some embodiments, quantitative PCR (qPCR) is utilized, e.g., using SYBR Green dye on an Applied Biosystems 7300 Real Time PCR system, or any other Real Time PCR system, essentially as described (Chinnaiyan et al., Cancer Res 65, 3328 (2005); Rubin et al., Cancer Res 64, 3814 (2004); herein incorporated by reference in its entirety).

In some embodiments, nucleic acid from a sample is sequenced (e.g., in order to detect biomarkers). Nucleic acid molecules may be sequence analyzed by any number of techniques. The analysis may identify the sequence of all or a part of a nucleic acid. Illustrative non-limiting examples of nucleic acid sequencing techniques include, but are not limited to, chain terminator (Sanger) sequencing and dye terminator sequencing, as well as "next generation" sequencing techniques. Those of ordinary skill in the art will recognize that because RNA is less stable in the cell and more prone to nuclease attack, experimentally RNA is usually, although not necessarily, reverse transcribed to DNA before sequencing.

A number of DNA sequencing techniques are known in the art, including fluorescence-based sequencing methodologies (See, e.g., Birren et al., Genome Analysis: Analyzing DNA, 1, Cold Spring Harbor, N.Y.; herein incorporated by reference in its entirety). In some embodiments, automated sequencing techniques understood in that art are utilized. In some embodiments, the systems, devices, and methods employ parallel sequencing of partitioned amplicons (PCT Publication No: WO2006084132 to Kevin McKernan et al., herein incorporated by reference in its entirety). In some embodiments, DNA sequencing is achieved by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques include the Church polony technology (Mitra et al., 2003, Analytical Biochemistry 320, 55-65; Shendure et al., 2005 Science 309, 1728-1732; U.S. Pat. No. 6,432,360, U.S. Pat. No. 6,485,944, U.S. Pat. No. 6,511,803; herein incorporated by reference in their entireties) the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. No. 6,787,308; U.S. Pat. No. 6,833,246; herein incorporated by reference in their entireties), the Lynx massively parallel signature sequencing technology (Brenner et al. (2000). Nat. Biotechnol. 18:630-634; U.S. Pat. No. 5,695,934; U.S. Pat. No. 5,714,330; herein incorporated by reference in their entireties) and the Adessi PCR colony technology (Adessi et al. (2000). Nucleic Acid Res. 28, E87; WO 00018957; herein incorporated by reference in its entirety).

A set of methods referred to as "next-generation sequencing" techniques have emerged as alternatives to Sanger and dye-terminator sequencing methods (Voelkerding et al., Clinical Chem., 55: 641-658, 2009; MacLean et al., Nature Rev. Microbiol., 7: 287-296; each herein incorporated by reference in their entirety). Next-generation sequencing (NGS) methods share the common feature of massively parallel, high-throughput strategies, with the goal of lower costs in comparison to older sequencing methods. NGS methods can be broadly divided into those that require template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, Pacific Biosciences (PAC BIO RS II) and other platforms commercialized.

In some embodiments, provided herein are methods for isolating DNA or RNA from a biological sample. Methods may comprise steps of homogenizing a sample in a suitable buffer, removal of contaminants and/or assay inhibitors adding a target capture reagent (e.g., a magnetic bead to which is linked an oligonucleotide complementary to the target), incubated under conditions that promote the association (e.g., by hybridization) of the target with the capture reagent to produce a target:capture reagent complex, incubating the target:capture complex under target-release conditions. In some embodiments, multiple biomarker targets are isolated in each round of isolation by adding multiple target capture reagents (e.g., specific to the desired biomarkers) to the solution. For example, multiple target capture reagents, each comprising an oligonucleotide specific for a different biomarker target can be added to the sample for isolation of multiple targets. It is contemplated that the methods encompass multiple experimental designs that vary both in the number of capture steps and in the number of targets captured in each capture step. In some embodiments, capture reagents are molecules, moieties, substances, or compositions that preferentially (e.g., specifically and selectively) interact with a particular biomarker sought to be isolated, purified, detected, and/or quantified. Any capture reagent having desired binding affinity and/or specificity to the analyte target can be used in the present technology. For example, the capture reagent can be a macromolecule such as a peptide, a protein (e.g., an antibody or receptor), an oligonucleotide, a nucleic acid, (e.g., nucleic acids capable of hybridizing with the target nucleic acids), vitamins, oligosaccharides, carbohydrates, lipids, or small molecules, or a complex thereof. As illustrative and non-limiting examples, an avidin target capture reagent may be used to isolate and purify targets comprising a biotin moiety, an antibody may be used to isolate and purify targets comprising the appropriate antigen or epitope, and an oligonucleotide may be used to isolate and purify a complementary oligonucleotide.

Any nucleic acids, including single-stranded and double-stranded nucleic acids, that are capable of binding, or specifically binding, to the target can be used as the capture reagent. Examples of such nucleic acids include DNA, RNA, aptamers, peptide nucleic acids, and other modifications to the sugar, phosphate, or nucleoside base. Thus, there are many strategies for capturing a target and accordingly many types of capture reagents are known to those in the art.

In addition, target capture reagents comprise a functionality to localize, concentrate, aggregate, etc. the capture reagent and thus provide a way to isolate and purify the target biomarker when captured (e.g., bound, hybridized, etc.) to the capture reagent (e.g., when a target:capture reagent complex is formed). For example, in some embodiments the portion of the target capture reagent that interacts with the target (e.g., the oligonucleotide) is linked to a solid support (e.g., a bead, surface, resin, column, and the like) that allows manipulation by the user on a macroscopic scale. Often, the solid support allows the use of a mechanical means to isolate and purify the target:capture reagent complex from a heterogeneous solution. For example, when linked to a bead, separation is achieved by removing the bead from the heterogeneous solution, e.g., by physical movement. In embodiments in which the bead is magnetic or paramagnetic, a magnetic field is used to achieve physical separation of the capture reagent (and thus the target) from the heterogeneous solution. Magnetic beads used to isolate targets are described in the art, e.g., as described in European Patent Application No. 87309308, incorporated herein in its entirety for all purposes.

In some embodiments, a computer-based analysis program is used to translate the raw data generated by the detection assay (e.g., the presence, absence, or amount of expression a panel of genes) into data of predictive value for a clinician (e.g., a risk score, a qualitative description, etc.). In some embodiments, data analysis produces a vulnerability score, responsiveness score, and/or remission score. In some embodiments, computer analysis combines the data from numerous biomarkers into a single score or value that is predictive and/or diagnostic for vulnerability score, responsiveness score, and/or remission score, respectively.

In some embodiments, a clinician accesses the data and/or analysis thereof using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information providers, medical personal, and subjects. For example, in some embodiments of the present invention, a sample (e.g., a biopsy or a blood or serum sample) is obtained from a subject and submitted to a profiling service (e.g., clinical lab at a medical facility, third-party testing service, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a blood sample, a urine sample, etc.) and directly send it to a profiling center. Where the sample also comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (e.g., expression data), specific for the diagnostic or prognostic information desired for the subject.

In some embodiments, profile data is prepared in a format suitable for interpretation by a treating clinician and/or the test subject. For example, rather than providing raw expression data, the prepared format may represent a diagnosis, risk, or likelihood assessment for the subject. Recommendations for particular treatment options may also be provided (e.g., psychoanalysis). The data may be displayed to the clinician by any suitable method. For example, in some embodiments, the profiling service generates a report that can be printed for the clinician (e.g., at the point of care) or displayed to the clinician on a computer monitor.

In some embodiments, a report is generated (e.g., by a clinician, by a testing center, by a computer or other automated analysis system, etc.). A report may contain test results, diagnoses, and/or treatment recommendations (e.g., psychoanalysis, psychotherapy, pharmaceutical treatment, observation, etc.).

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may choose further intervention, treatment, and/or counseling based on the results. In some embodiments, the data is used for research use. For example, the data may be used to further optimize the inclusion or elimination of markers as more or less useful (e.g., in a particular population (e.g., children, adolescents, adults, males, females, etc.).

Compositions for use in the methods of the present invention include, but are not limited to, probes, amplification oligonucleotides, and antibodies. Particularly preferred compositions detect the level of expression (e.g., blood mRNA level, blood protein level) of a panel of genes. Systems and kits are provided that are useful, necessary, and/or sufficient for detecting expression of one or more genes. Any of these compositions, alone or in combination with other compositions of the present invention, may be provided in the form of a kit or reagent mixture. For example, labeled probes and primer pairs are provided in a kit for the amplification and detection and/or quantification of a panel of genes comprising one or more biomarkers described herein. Kits may include any and all components necessary or sufficient for assays including, but not limited to, detection reagents, amplification reagents, buffers, control reagents (e.g., tissue samples, positive and negative control sample, etc.), solid supports, labels, written and/or pictorial instructions and product information, inhibitors, labeling and/or detection reagents, package environmental controls (e.g., ice, desiccants, etc.), and the like. In some embodiments, kits provide a sub-set of the required components, wherein it is expected that the user will supply the remaining components. In some embodiments, the kits comprise two or more separate containers wherein each container houses a subset of the components to be delivered.

In some embodiments, the present invention provides therapies for diseases characterized by altered expression of disease markers identified using the methods of the present invention. In particular, the present invention provides methods and compositions for monitoring the effects of a candidate therapy and for selecting therapies for patients.

In some embodiments, methods of treating depression are provided (e.g., following detection/quantification of one or more of the vulnerability, responsiveness, and/or remission biomarker panels for described herein). Suitable treatments include psychotherapy; medication (e.g., selective serotonin reuptake inhibitors (SSRIs) (e.g., fluoxetine (Prozac), paroxetine (Paxil), sertraline (Zoloft), citalopram (Celexa) and escitalopram (Lexapro), etc.), serotonin and norepinephrine reuptake inhibitors (SNRIs) (e.g., duloxetine (Cymbalta), venlafaxine (Effexor XR) and desvenlafaxine (Pristiq), etc.), norepinephrine and dopamine reuptake inhibitors (NDRIs) (e.g., Bupropion (Wellbutrin), etc.), atypical antidepressants (e.g., trazodone, mirtazapine (Remeron), vilazodone (Viibryd), etc.), tricyclic antidepressants (e.g., imipramine (Tofranil) and nortriptyline (Pamelor), etc.), monoamine oxidase inhibitors (MAOIs) (e.g., tranylcypromine (Parnate), phenelzine (Nardil), etc.), mood stabilizers, antipsychotics, anti-anxiety medications, stimulant medications, etc.); hospitalization or residential treatment; electroconvulsive therapy (ECT); transcranial magnetic stimulation (TMS); etc.

In some embodiments, systems and devices are provided for implementing the diagnostic methods described herein (e.g., data analysis, communication, result reporting, etc.). In some embodiments, a software or hardware component receives the results of multiple assays, factors, and/or biomarkers and determines a single value result to report to a user that indicates a conclusion related to vulnerability (e.g., highly vulnerable to recurrent depression, low risk of recurrent depression, etc.), responsiveness to psychotherapy (e.g., highly response, moderately response, likely nonresponsive), and/or remission following psychotherapy (e.g., in remission, not in remission). Related embodiments calculate a risk factor based on a mathematical combination (e.g., a weighted combination, a linear combination) of the results from multiple assays, factors, and/or biomarkers.

Some embodiments comprise a storage medium and memory components. Memory components (e.g., volatile and/or nonvolatile memory) find use in storing instructions (e.g., an embodiment of a process as provided herein) and/or data. Some embodiments relate to systems also comprising one or more of a CPU, a graphics card, and a user interface (e.g., comprising an output device such as display and an input device such as a keyboard). Programmable machines associated with the technology comprise conventional extant technologies and technologies in development or yet to be developed (e.g., a quantum computer, a chemical computer, a DNA computer, an optical computer, a spintronics based computer, etc.). In some embodiments, the technology comprises a wired (e.g., metallic cable, fiber optic) or wireless transmission medium for transmitting data. For example, some embodiments relate to data transmission over a network (e.g., a local area network (LAN), a wide area network (WAN), an ad-hoc network, the internet, etc.). In some embodiments, programmable machines are present on such a network as peers and in some embodiments the programmable machines have a client/server relationship. In some embodiments, data are stored on a computer-readable storage medium such as a hard disk, flash memory, optical media, a floppy disk, etc.

In some embodiments, the technology provided herein is associated with a plurality of programmable devices that operate in concert to perform a method as described herein. For example, in some embodiments, a plurality of computers (e.g., connected by a network) may work in parallel to collect and process data, e.g., in an implementation of cluster computing or grid computing or some other distributed computer architecture that relies on complete computers (with onboard CPUs, storage, power supplies, network interfaces, etc.) connected to a network (private, public, or the internet) by a conventional network interface, such as Ethernet, fiber optic, or by a wireless network technology.

Some embodiments provide a computer that includes a computer-readable medium. The embodiment includes a random access memory (RAM) coupled to a processor. The processor executes computer-executable program instructions stored in memory. Such processors may include a microprocessor, an ASIC, a state machine, or other processor, and can be any of a number of computer processors, such as processors from Intel Corporation of Santa Clara, Calif. and Motorola Corporation of Schaumburg, Ill. Such processors include, or may be in communication with, media, for example computer-readable media, which stores instructions that, when executed by the processor, cause the processor to perform the steps described herein.

Embodiments of computer-readable media include, but are not limited to, an electronic, optical, magnetic, or other storage or transmission device capable of providing a processor with computer-readable instructions. Other examples of suitable media include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any suitable computer-programming language, including, for example, C, C++, C#, Visual Basic, Java, Python, Perl, and JavaScript.

Computers are connected in some embodiments to a network. Computers may also include a number of external or internal devices such as a mouse, a CD-ROM, DVD, a keyboard, a display, or other input or output devices. Examples of computers are personal computers, digital assistants, personal digital assistants, cellular phones, mobile phones, smart phones, pagers, digital tablets, laptop computers, internet appliances, and other processor-based devices. In general, the computers related to aspects of the technology provided herein may be any type of processor-based platform that operates on any operating system, such as Microsoft Windows, Linux, UNIX, Mac OS X, etc., capable of supporting one or more programs comprising the technology provided herein. Some embodiments comprise a personal computer executing other application programs (e.g., applications). The applications can be contained in memory and can include, for example, a word processing application, a spreadsheet application, an email application, an instant messenger application, a presentation application, an Internet browser application, a calendar/organizer application, and any other application capable of being executed by a client device.

All such components, computers, and systems described herein as associated with the technology may be logical or virtual.

EXPERIMENTAL

Participant characteristics are described in Table 1. Patients with MDD were treated with 18 sessions of CBT administered either face-to-face or by telephone by a PhD level psychologist. These methods of treatment administration produced equivalent outcomes for depression (Mohr et al., 2012; herein incorporated by reference in its entirety).

TABLE 1

Baseline and follow-up sample characteristics

|  | Sex | Age | Caucasian (%) | HAM-D baseline | PHQ9 baseline | Post-CBT PHQ9 | | | |
|---|---|---|---|---|---|---|---|---|---|
|  |  |  |  |  |  | Remitted (N = 11) | | Not remitted (N = 16) | |
| Patients | F(N = 22) | 48.9 ± 16.1 | 17(77%) | 23.6 ± 3.7 | 18.8 ± 4.1 | N = 7 | 1.29 ± 1.5 | N = 10 | 12.9 ± 5.0 |
| (N = 32) | M(N = 10) | 50.3 ± 13.6 | 8(80%) | 22.5 ± 4.4 | 16.6 ± 4.7 | N = 4 | 4.3 ± 1.0 | N = 6 | 11.0 ± 3.6 |
| Controls | F(N = 24) | 48.5 ± 15.6 | 16(73%) | 4.2 ± 2.5 | 0.2 ± 0.5 | — | | — | |
| (N = 32) | M(N = 10) | 53.6 ± 14.6 | 8(80%) | 4.1 ± 2.0 | 0.1 ± 0.3 | — | | — | |
|  |  |  |  |  |  | Remitted (N = 9) | | Not remitted (N = 13) | |
| With week 18 | F(N = 13) | 52.1 ± 16.6 | 11(85%) | 23.3 ± 3.8 | 18.2 ± 3.6 | N = 5 | 1.00 ± 1.0 | N = 8 | 12.38 ± 5.3 |

TABLE 1-continued

Baseline and follow-up sample characteristics

| | Sex | Age | Caucasian (%) | HAM-D baseline | PHQ9 baseline | Post-CBT PHQ9 | | | |
|---|---|---|---|---|---|---|---|---|---|
| blood draw (N = 22) | M(N = 9) | 50.9 ± 14.3 | 7(78%) | 22.8 ± 4.6 | 16.6 ± 5.0 | N = 4 | 4.25 ± 1.0 | N = 5 | 10.6 ± 3.8 |
| | | | | | | Remitted (N = 2) | | Not remitted (N = 3) | |
| Without week 18 blood draw (N = 10) | F(N = 9) | 44.3 ± 15.1 | 6(67%) | 23.9 ± 3.7 | 19.6 ± 4.9 | N = 2 | 2.0 ± 2.8 | N = 2 | 15.0 ± 4.2 |
| | M(N = 1) | 45.0 | 1(100%) | 20.0 | 17.0 | — | — | N = 1 | 13.0 |

Major depressive disorder (MDD) diagnosis was evaluated at baseline and post-treatment (week 18) using the Mini-International Neuropsychiatric Interview (MINI). Depression severity was evaluated by self-report using the PHQ-9 at baseline and post-treatment. Because patients who no longer reach criteria for MDD at post-treatment may still experience significant symptoms, patients were also classified as reaching full remission based on the MacArthur criterion of PHQ-9<5 (The MacArthur Foundation's Initiative on Depression and Primary Care. 2004; herein incorporated by reference in its entirety). Bloods were also drawn at baseline and post-treatment.

Whole blood RNA was isolated using the PAXgene Blood RNA Kit (Qiagen Inc.) according to the manufacturer's instruction; cDNA was prepared using random primers and the TaqMan RT reagents (ABI). For the microarray study, RNA was extracted from blood samples of 12 subjects before and after CBT. Illumina HumanHT 12 array was employed. Quantitative real time PCR (qPCR) was carried out using SYBR Green and the ABI 7900 (Applied Biosystems, Foster City, Calif.), with 18s rRNA as the internal control. 18s was chosen as the normalizing gene after an extensive comparative pilot study using several housekeeping genes. Each sample for each transcript was measured in triplicate using 5 ng of template.

In the subsequent statistical analyses, ACT values from qPCR were used to characterize transcript abundance, where ACT is the cycle threshold difference between the target gene and the housekeeping gene, which in this case is 18s. Some of the statistical analyses took advantage of the control matching design and ACT values of MDD subject to that of the matching No Disorder (ND) control (1). The fold change, therefore, was relative to age-, gender-, and race-matched controls, and defined as relative quantification (RQ).

Baseline PHQ-9, HamD, and ACT transcript expressions were compared between MDD and ND using Wilcoxon signed rank tests, and presented with mean and standard deviation. Baseline RQ expression least squared means were estimated and compared between those who were in clinical remission (PHQ9≤5) by week 18 and those who remained depressed, using mixed models, adjusting for age, sex and race. Q-values were calculated with Benjamini and Hochberg methodology (Benjamini and Hochberg, 1995; herein incorporated by reference in its entirety) using q value package (Storey and Tibshirani, 2003; herein incorporated by reference in its entirety) in R (R Development Core Team, 2009; herein incorporated by reference in its entirety).

A. Vulnerability Biomarkers

Experiments were conducted during development of embodiments of the present invention to identify biomarkers with distinct blood transcript levels between subjects with MDD and control subject (without MDD or recurrent depression) regardless of current clinical diagnosis. Both baseline and post-CBT blood transcript levels of subjects with MDD were compared to No Disorder control levels. Significant differences were seen in DGKA, IGSF4A/CADM1, KIAA1539, MARCKS, and RAPH1 blood transcript levels at both time points, while ADCY3, FAM46A, PSME1 and TLR7 were only significant at baseline (Tables 2 and 3).

TABLE 2

Baseline transcript levels (ΔCT) for subjects with MDD (N = 32) and sex, age, race matched ND controls (N = 32).

| Gene | MDD Mean (SD) | CONTROL Mean (SD) | p-value | q | Cohen's D |
|---|---|---|---|---|---|
| ADCY3 | 20.95(2.07) | 21.31(2.18) | 0.012 | 0.026 | 0.473 |
| AMFR | 19.28(0.87) | 19.27(0.42) | 0.995 | 0.995 | 0.001 |
| ASAH1 | 16.74(2.45) | 16.88(2.25) | 0.352 | 0.503 | 0.167 |
| ATP11C | 19.22(1.83) | 19.20(2.17) | 0.902 | 0.949 | 0.022 |
| CD59 | 19.98(0.65) | 19.89(0.66) | 0.550 | 0.651 | 0.107 |
| CDR2 | 20.60(1.13) | 20.49(0.65) | 0.554 | 0.652 | 0.106 |
| CMAS | 22.41(1.36) | 22.98(0.69) | 0.046 | 0.084 | 0.367 |
| DGKA | 16.69(0.80) | 17.41(0.75) | 0.000 | 0.003 | 0.730 |
| FAM46A | 19.65(2.27) | 19.96(2.40) | 0.005 | 0.017 | 0.532 |
| IGSF4A/CADM1 | 22.22(3.07) | 23.05(2.57) | 0.002 | 0.010 | 0.597 |
| KIAA1539 | 18.22(0.61) | 18.64(0.45) | 0.001 | 0.009 | 0.625 |
| MAF | 22.00(2.31) | 22.08(2.47) | 0.637 | 0.708 | 0.084 |
| MARCKS | 16.85(2.31) | 17.41(2.22) | 0.005 | 0.017 | 0.533 |
| NAGA | 17.63(2.22) | 17.85(2.30) | 0.041 | 0.083 | 0.376 |
| PSME1 | 17.17(0.75) | 17.55(0.52) | 0.008 | 0.023 | 0.501 |
| PTP4A3 | 20.79(0.82) | 21.03(0.62) | 0.154 | 0.257 | 0.258 |
| RAPH1 | 21.73(1.47) | 22.80(0.54) | <0.001 | 0.003 | 0.737 |
| SLC4A1 | 17.08(0.85) | 17.22(0.85) | 0.454 | 0.606 | 0.134 |
| TLR7 | 19.53(2.36) | 19.89(2.35) | 0.009 | 0.023 | 0.493 |
| ZNF291 | 23.55(3.18) | 23.20(3.20) | 0.176 | 0.270 | 0.253 |

TABLE 3

Post-treatment transcript levels (ΔCT) for subjects with MDD (N = 22) and sex, age, race matched ND controls (N = 22).

| Gene | MDD Mean (SD) | CONTROL Mean (SD) | P-value | q | Cohen's D |
|---|---|---|---|---|---|
| ADCY3 | 20.25(1.85) | 20.44(1.96) | 0.092 | 0.190 | 0.357 |
| AMFR | 19.33(0.75) | 19.33(0.47) | 0.913 | 0.913 | 0.004 |
| ASAH1 | 15.98(2.15) | 16.04(2.13) | 0.680 | 0.716 | 0.065 |
| ATP11C | 18.78(2.13) | 18.48(2.11) | 0.123 | 0.208 | 0.363 |
| CD59 | 20.09(0.67) | 19.79(0.74) | 0.125 | 0.208 | 0.355 |
| CDR2 | 20.68(1.23) | 20.46(0.66) | 0.376 | 0.470 | 0.215 |
| CMAS | 22.55(1.04) | 23.04(0.70) | 0.076 | 0.190 | 0.481 |
| DGKA | 16.33(0.72) | 17.40(0.89) | <.001 | 0.005 | 0.883 |
| FAM46A | 18.84(2.18) | 19.04(2.22) | 0.232 | 0.331 | 0.309 |
| IGSF4A/CADM1 | 21.50(2.48) | 22.19(2.48) | 0.001 | 0.005 | 0.862 |
| KIAA1539 | 18.15(0.62) | 18.71(0.50) | <.001 | 0.005 | 0.840 |
| MAF | 21.16(2.11) | 21.10(2.33) | 0.555 | 0.653 | 0.026 |
| MARCKS | 16.22(1.82) | 16.64(2.12) | 0.010 | 0.040 | 0.558 |
| NAGA | 16.89(2.15) | 16.99(2.14) | 0.595 | 0.661 | 0.119 |

TABLE 3-continued

Post-treatment transcript levels (ΔCT) for subjects with MDD (N = 22) and sex, age, race matched ND controls (N = 22).

| Gene | MDD Mean (SD) | CONTROL Mean (SD) | P-value | q | Cohen's D |
|---|---|---|---|---|---|
| PSME1 | 17.04(0.68) | 17.46(0.56) | 0.033 | 0.094 | 0.533 |
| PTP4A3 | 20.79(0.74) | 21.05(0.64) | 0.163 | 0.251 | 0.339 |
| RAPH1 | 21.45(1.07) | 22.86(0.60) | <.001 | 0.005 | 1.086 |
| SLC4A1 | 17.02(1.16) | 17.37(0.80) | 0.095 | 0.190 | 0.290 |
| TLR7 | 18.52(2.24) | 18.92(2.09) | 0.016 | 0.533 | 0.550 |
| ZNF291 | 22.48(3.12) | 21.95(2.96) | 0.373 | 0.470 | 0.249 |

Expression of DGKA, KIAA1539 and RAPH1 differed between patients with MDD regardless of their depression diagnostic status with high specificity and selectivity. Table 4 shows results of the ROC analyses.

TABLE 4

Receiver operating characteristics for post-CBT measures of blood transcript levels (ΔCt).

| Gene | AUC | Std. Error | P | P(t-test) |
|---|---|---|---|---|
| RAPH1 remitted | 0.952 | 0.036 | <0.0001 | <0.0001 |
| RAPH1 not-remitted | 0.867 | 0.059 | 0.0003 | <0.0001 |
| KIAA1539 remitted | 0.826 | 0.079 | 0.003 | 0.0017 |
| KIAA1539 not-remitted | 0.701 | 0.095 | 0.048 | 0.0179 |
| DGKA remitted | 0.878 | 0.061 | 0.0006 | 0.0002 |
| DGKA not-remitted | 0.796 | 0.073 | 0.0036 | 0.002 |

B. Remission Biomarkers

Experiments were conducted during development of embodiments of the present invention to identify biomarkers with distinct blood transcript levels between subjects with MDD who remitted after 18 weeks of CBT and those who remained clinically depressed following CBT (e.g., relapsed). Post-CBT blood transcript levels, normalized to age, gender, race-matched controls, were compared between subjects remitted from MDD at week 18 post-treatment and those who did not. Blood transcript levels of ASAH1, ATP11C, KIAA1539 and PSME1 differed significantly, while MARCKS tended to differ between patients who remitted and those who did not remit in response to CBT (Table 5).

Experiments were also conducted using blood samples from 12 subjects collected before and after CBT. Subjects were 3 males and 9 females, 8 non-Hispanic whites, 2 Hispanic whites and 2 African Americans. RNA was extracted from blood samples as before. Samples were analyzed on Illumina HumanHT 12 bead array. Gene expression differences between the two time points were analyzed and DRD2, OSBPL2, DAG1, OTX2, DPPA3, RAB27B, CTTNBP2, LIX1, NTRK2 and SLC24A4 were found to change significantly in subjects who remitted post-CBT.

TABLE 5

Adjusted post treatment LS means expressions (RQ) among MDD patients by remission status.

| Gene | PHQ9 > 5 (N = 13) RQ mean (SE) | PHQ9 <= 5 (N = 9) RQ mean (SE) | F-test p | Adjusted for age, sex, race p-value |
|---|---|---|---|---|
| ADCY3 | 1.52(0.22) | 1.47(0.22) | 0.404 | 0.879 |
| AMFR | 1.33(0.24) | 1.47(0.25) | 0.417 | 0.669 |
| ASAH1 | 0.90(0.12) | 1.38(0.12) | 0.032 | 0.009 |
| ATP11C | 1.12(0.16) | 0.62(0.16) | 0.486 | 0.035 |
| CD59 | 0.92(0.15) | 1.13(0.16) | 0.099 | 0.316 |
| CDR2 | 1.54(0.26) | 1.22(0.27) | 0.532 | 0.377 |
| CMAS | 2.13(0.64) | 2.69(0.68) | 0.099 | 0.523 |
| DGKA | 3.56(0.92) | 3.78(0.92) | 0.863 | 0.403 |
| FAM46A | 1.41(0.23) | 1.20(0.23) | 0.964 | 0.518 |
| IGSF4A | 1.60(0.44) | 2.08(0.44) | 0.275 | 0.433 |
| KIAA1539 | 1.72(0.21) | 2.34(0.22) | 0.074 | 0.042 |
| MAF | 1.08(0.21) | 1.09(0.21) | 0.526 | 0.963 |
| MARCKS | 1.26(0.33) | 2.18(0.33) | 0.085 | 0.058 |
| NAGA | 1.25(0.21) | 1.28(0.21) | 0.434 | 0.91 |
| PSME1 | 1.70(0.30) | 2.30(0.31) | 0.017 | 0.148 |
| PTP4A3 | 1.52(0.25) | 1.95(0.26) | 0.206 | 0.079 |
| RAPH1 | 4.30(1.29) | 5.49(1.36) | 0.116 | 0.504 |
| SLC4A1 | 1.70(0.52) | 2.47(0.54) | 0.298 | 0.279 |
| TLR7 | 1.77(0.29) | 1.76(0.29) | 0.418 | 0.979 |
| ZNF291 | 1.39(0.44) | 1.21(0.44) | 0.285 | 0.771 |

C. Responsiveness Biomarkers

Experiments were conducted during development of embodiments of the present invention to identify biomarkers with distinct blood transcript levels, prior to treatment, between subjects responsive to treatment and those who are unresponsive. There were numerous and highly significant gene expression correlations at baseline, but none of these were significant at post-CBT. A similar pattern emerged when the interactions by response status (remission at post-treatment) was analyzed. The correlations between transcript levels at baseline in the separate cohorts of MDD subjects showed that blood transcript levels of RAPH1, PSME1, IGSF4A, ADCY3, FAM46A and DGKA differ in parallel in MDD patients compared to controls in those who remitted after post-CBT, but not in those who remained clinically depressed.

All publications and patents provided herein incorporated by reference in their entireties. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

I claim:

1. A panel of biomarkers consisting of an isolated set of 100 or fewer full-length cDNA biomarkers, wherein said isolated set includes DGKA, RAPH1, and KIAA1539 full-length cDNA biomarkers.

2. The panel of biomarkers of claim 1, comprising a full-length DRD2 cDNA biomarker.

3. The panel of biomarkers of claim 1, comprising a full-length OSBPL2 cDNA biomarker.

4. The panel of biomarkers of claim 1, comprising a full-length DAG1 cDNA biomarker.

5. The panel of biomarkers of claim 1, comprising a full-length OTX2 cDNA biomarker.

6. The panel of biomarkers of claim 1, comprising a full-length DPPA3 cDNA biomarker.

7. The panel of biomarkers of claim 1, comprising a full-length RAB27B cDNA biomarker.

8. The panel of biomarkers of claim 1, a full-length CTTNBP2 cDNA biomarker.

9. The panel of biomarkers of claim 1, comprising a full-length LIX1 cDNA biomarker.

10. The panel of biomarkers of claim 1, comprising a full-length NTRK2 cDNA biomarker.

11. The panel of biomarkers of claim 1, comprising a full-length SLC24A4 cDNA biomarker.

12. The panel of biomarkers of claim 1, comprising a full-length MARCKS cDNA biomarker.

13. The panel of biomarkers of claim 1, comprising a full-length ASAH1 cDNA biomarker.

14. The panel of biomarkers of claim 1, comprising a full-length ATP11C cDNA biomarker.

15. The panel of biomarkers of claim 1, comprising a full-length PSME1 cDNA biomarker.

16. The panel of biomarkers of claim 1, comprising a full-length IGSF4A cDNA biomarker.

17. The panel of biomarkers of claim 1, comprising a full-length ADCY3 cDNA biomarker.

18. The panel of biomarkers of claim 1, comprising full-length FAM46A cDNA biomarker.

\* \* \* \* \*